United States Patent [19]

Riall et al.

[11] Patent Number: 5,753,512
[45] Date of Patent: May 19, 1998

[54] DETERMINING LIQUID VOLUMES IN CUP-LIKE VESSELS ON A ROTOR HAVING VERTICAL DEVIATIONS

[75] Inventors: James Daniel Riall, Pittsford; David Donald Hyde, Ontario, both of N.Y.

[73] Assignee: Johnson & Johnson Clinical Diagnostics, inc. Rochester, N.Y.

[21] Appl. No.: 748,306

[22] Filed: Nov. 13, 1996

[51] Int. Cl.$^6$ ................................. G01N 35/10
[52] U.S. Cl. .................... 436/50; 436/49; 436/54; 436/180; 422/64; 422/67; 422/100; 73/864.11; 73/863.01
[58] Field of Search .................. 436/43, 47, 48, 436/49, 50, 54, 55, 180; 422/63, 64, 67, 81, 100; 73/863.01, 864.11

[56] References Cited

U.S. PATENT DOCUMENTS

| | | | |
|---|---|---|---|
| 4,794,085 | 12/1988 | Jessop et al. | 436/54 |
| 5,013,529 | 5/1991 | Itoh | 422/100 |
| 5,133,392 | 7/1992 | Hamann | 141/1 |
| 5,244,633 | 9/1993 | Jakubowicz et al. | 422/64 |
| 5,270,210 | 12/1993 | Weyrauch et al. | 436/43 |
| 5,319,964 | 6/1994 | Stephenson et al. | 73/149 |
| 5,389,339 | 2/1995 | Petschek et al. | 422/64 |
| 5,443,791 | 8/1995 | Cathcart et al. | 422/65 |

*Primary Examiner*—Long V. Le
*Attorney, Agent, or Firm*—Dana M. Schmidt

[57] ABSTRACT

Method and apparatus for determining actual liquid volumes in vessels in an incubator rotor that experiences vertical run-out as it rotates past stations that fill the vessels with liquid. Air pressure is used to determine the height of the bottom of each of the empty vessels, and then the height of the liquid that fills the vessels, so that the difference in height is converted into volume to compare with the desired and expected volume for the operation that does the volume-filling.

3 Claims, 6 Drawing Sheets

DETERMINING LIQUID VOLUMES IN CUP-LIKE VESSELS ON A ROTOR HAVING VERTICAL DEVIATIONS

FIELD OF THE INVENTION

This invention relates to a method and apparatus for verifying the vertical location of cup-like vessels on a rotor in an analyzer, and for thereby ascertaining the actual amount of liquid that ends up being placed in such containers.

BACKGROUND OF THE INVENTION

It is known in wet assay analyzers, to determine the volume of liquid in a container by calculating the bottom height of an empty container from a reference surface, filling the container, sensing the height of the liquid-air interface of the filled container, and calculating the volume from the differences in height. This is taught, for example, in U.S. Pat. No. 5,443,791, column 8, lines 44–47, wherein non-contact capacitance sensing is used. However, in this case a gauge block 24 "in one corner of the work area", column 9, lines 3–4, is the basis for an a priori assignment of the height of the bottom of the empty container. Lines 11–14 state that all stations are accurately registered with respect to the work surface and gauge block, allowing an assumption to be made that the height of the bottom of the empty container never varies.

In systems using rotors to mount the containers, the aforesaid assumption may turn out to be invalid. Indeed, in twin rotor incubators such as those taught for the analyzers of U.S. Pat. No. 5,244,633, extensive vertical run-out can occur so that the height of the bottom of an empty container can easily vary, container to container, even if that height is sensed at a singular fixed circumferential position passed by the rotor. Hence, in such a case, merely sensing the height of the liquid after the container is filled, gives no assurance of the volume of the liquid. Such volumes become important in certain assays, such as those that have a wash and soak cycle requiring an accurate and small volume of wash liquid. If the error allowed in such soak volumes is only ±10 µL out of 230 µL, it is easily possible for the rotor vertical run-out to create an error of as much as ±5 µL, which is 50% of the allowed error. The smaller the volume that is used, the smaller the error volumes that are possible. This use of 50% of the allowed error leaves too little error tolerance for other factors in the analyzer.

There has been a need, therefore, prior to this invention, to ascertain empty and full heights of each container on a rotor, independently of any fixed reference site not associated with the rotor. Particularly this has been a need when operating with small volumes of liquid which in turn are preferred for reduction in overall costs.

RELATED APPLICATION

A related pending application, co-filed herewith by the same inventors, is U.S. Ser. No. 08/747,878, entitled "DETERMINING HEIGHT VARIATIONS AROUND A ROTOR", Attorney Docket No. CDS0129. That application claims a divisible aspect disclosed but not claimed herein, that is, a method for the determination of height variations of the vessels described herein in the rotor of the analyzer described herein.

SUMMARY OF THE INVENTION

We have constructed a method for making volumetric determinations for containers mounted on a rotor subject to vertical run-out.

More specifically, in accord with one aspect of the invention, there is provided a method of determining the volume of liquid added to a cup-like reaction vessel of known dimensions, comprising the steps of:

a) positioning the vessel in a movable support;

b) moving the support and vessel until the vessel is at a sensing station;

c) sensing the vertical position of the bottom inside surface of the vessel at the sensing station using a sensor;

d) moving the support and vessel to a liquid-adding station;

e) adding a volume of liquid to the vessel at the liquid-adding station, leaving an air-liquid interface at the top of the volume;

f) moving the support and vessel until the vessel is returned to said sensing station;

g) sensing the vertical position of the interface at the sensing station using the sensor; and h) converting the sensed vertical positions of the bottom surface and the interface into a volume measurement of the liquid volume.

In accord with yet another aspect of the invention, there is provided apparatus for determining the volume of liquid added to a cup-like reaction vessel of known dimensions, comprising the steps of:

a rotor support with openings therein that mount a plurality of cup-like reaction vessels;

a plurality of stations disposed around the circumference of the rotor, including a wash station;

a motor that rotates the rotor and containers between the stations;

a sensor independent of the wash station and which is also disposed at a position on the circumference; the sensor sensing the height of an air-solid or air-liquid interface of the containers without contacting the interface;

means for pivoting the sensor over and down into a container on the rotor; and a computer for recording heights sensed by the sensor and for converting the heights into a liquid volume measurement.

Accordingly, it is an advantageous feature of the invention that the liquid volume of each container on a rotor can be accurately ascertained, even in the presence of an unpredictable vertical run-out in the rotor.

It is a related advantageous feature of the invention that such volume can be ascertained apart from the probe that is used to fill the volume, as a check on the reliability of that probe.

Other advantageous features will become apparent upon reference to the Detailed Description that follows, when read in light of the attached drawings.

DESCRIPTION OF THE PREFERRED EMBODIMENTS

The invention is described in connection with certain preferred embodiments, in which the reaction vessel is a cup, the movable support is a rotor, the air pressure for the sensing comes from a pump, the critical station along the rotor for vertical height determination is a cup-wash station, and when the wash probe is also used as a sensing probe, the air pressure is protected from the wash liquid by a one-way ball valve. In addition, the invention is applicable for vessels other than cups; movable supports of any kind susceptible to a vertical run-out; sources of air pressure other than pumps (for example, a source of inexhaustible constant pressure); height sensing at critical stations other than the cup-wash station; and combined sensor-wash probes using one-way protective valves other than a ball valve. As noted the invention is particularly useful when using small liquid soak volumes. As used herein, "small volume" means, no greater than about 250 µL.

Figure 1:
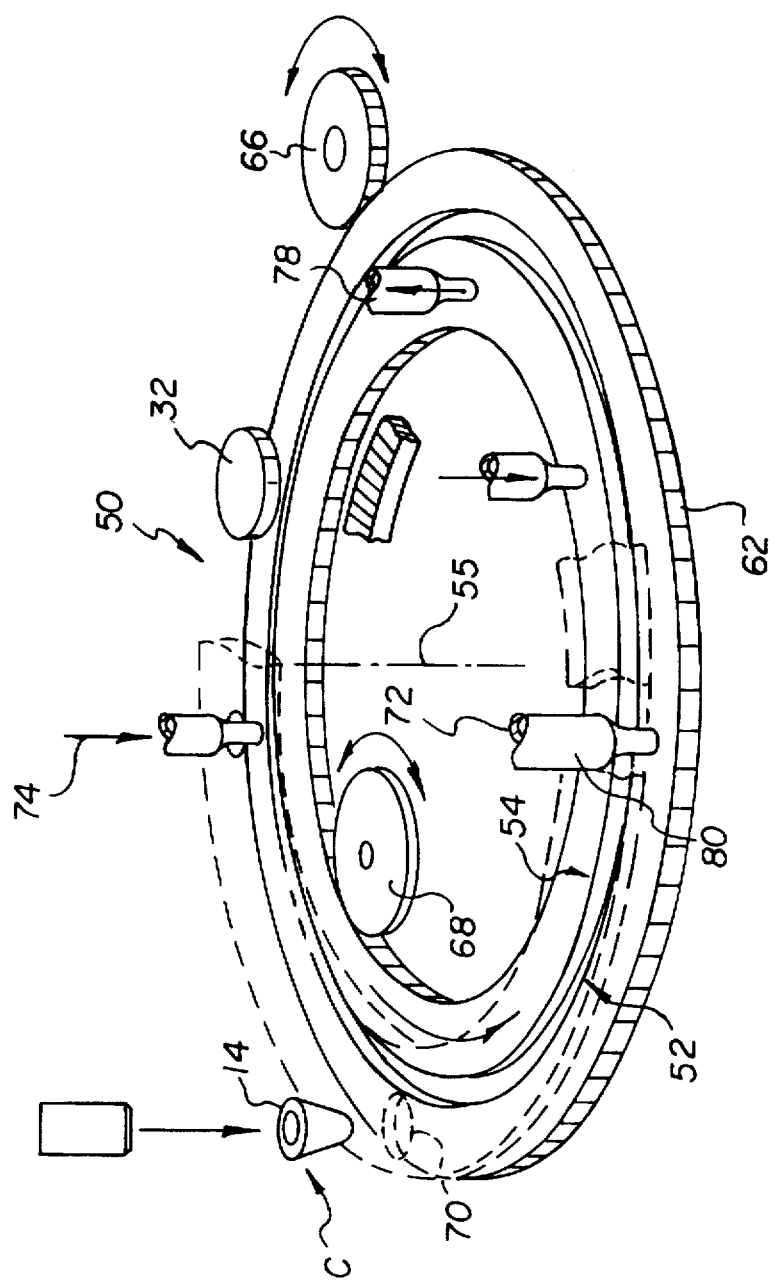
FIG. 1 is a partially schematic, fragmentary isometric view of the incubator of an analyzer with which the invention is useful.

Preferably, FIG. 1, the invention is used in an analyzer featuring an incubator 50 using at least one rotor 52 or 54 to support cups or vessels C therein at apertures 70, delivered from a cuvette-loading station 14. Most preferably, it is used with respect to the innermost rotor 54 at or adjacent to wash probe 78, as described hereinafter. Rotors 52 and 54 are driven by gears 66 and 68, respectively, around axis 55, and various other steps in the analysis of the sample in vessels C are performed at the other stations 74, 80, and luminometer 32, all as described in detail in, e.g., U.S. Pat. No. 5,244,633, the details of which are expressly incorporated herein by reference.

Figure 2:
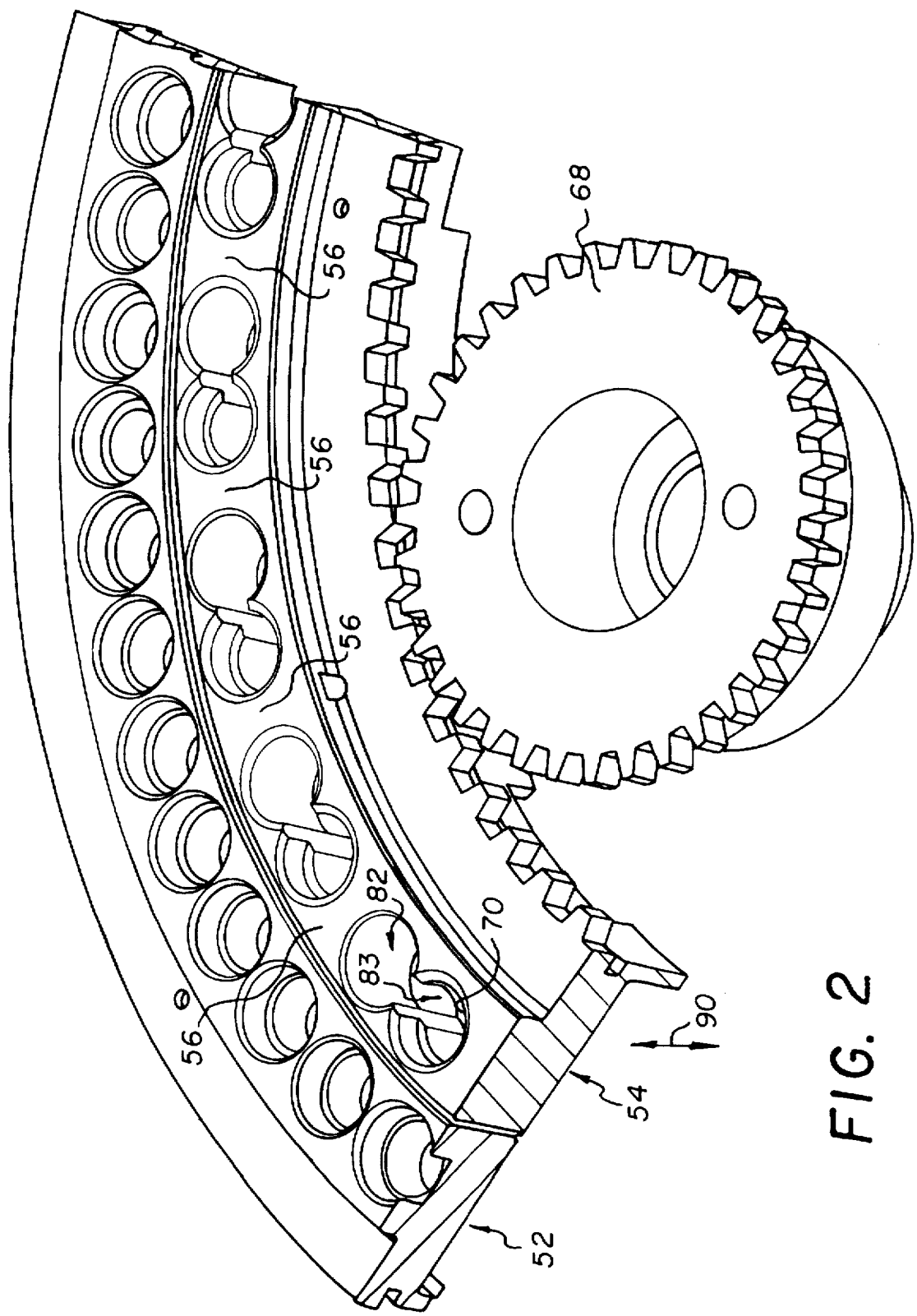
FIG. 2 is a fragmentary isometric view similar to FIG. 1, enlarged to show more details.

Most preferably, rotor 54 is as shown in FIG. 2 and as described in U.S. Pat. No. 5,456,883, wherein each vessel-holding aperture 70 intersects a paired dump aperture 82 with a narrow passageway 83 connecting them. (Only one such pair is labeled, for clarity.) The details of said '883 patent are also expressly incorporated herein by reference. Each pair of apertures 70 & 82 is spaced away from the adjacent pair by a generally horizontal top surface 56, the utility of which will become apparent.

Figure 3:
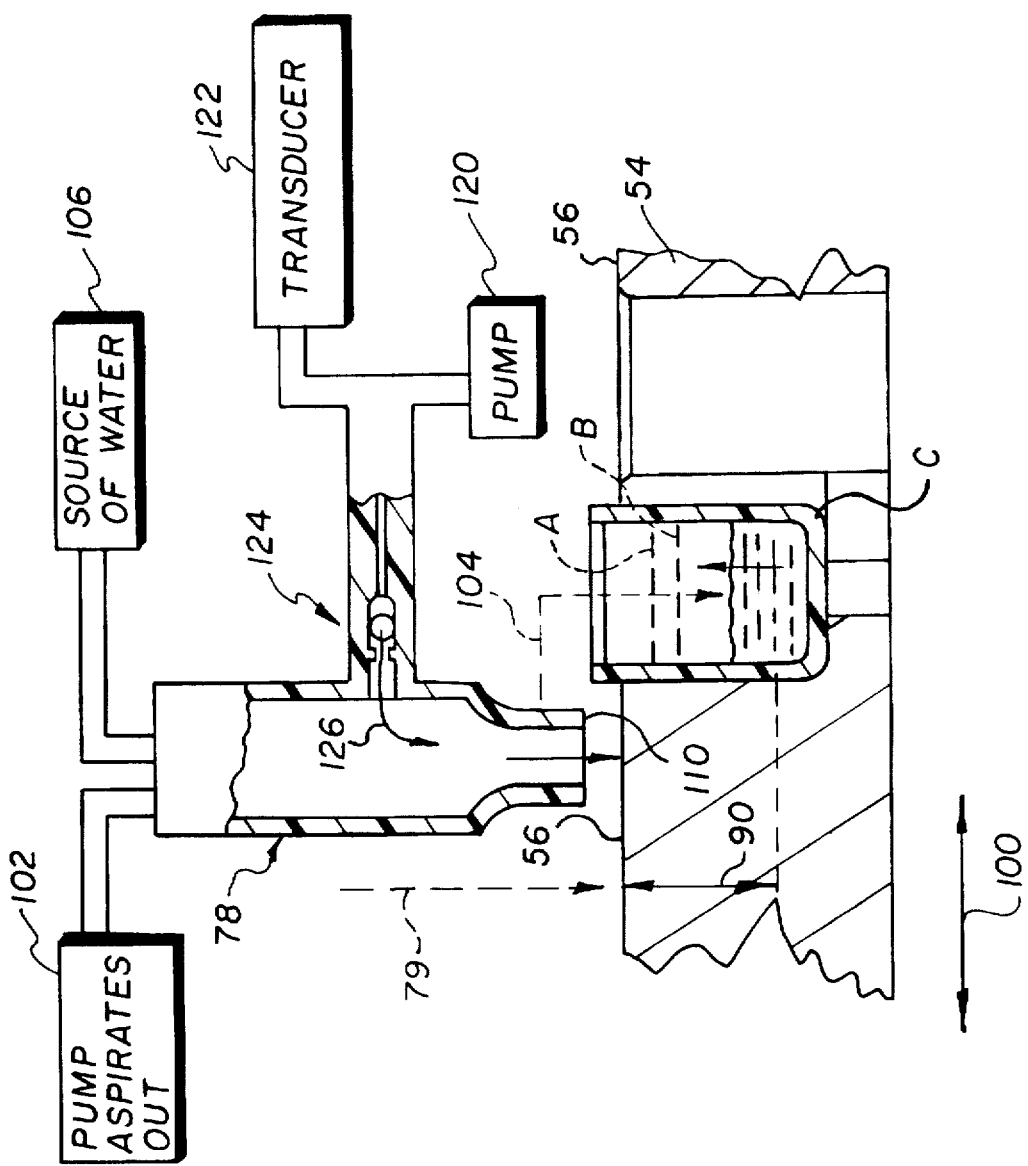
FIG. 3 is a fragmentary elevational view in section of the rotor and one embodiment of the invention.

The problem to be overcome by the invention is the vertical run-out of rotor 54 as it is rotated by gear 68. Such vertical run-out produces Z-axis vertical deviations, shown as double arrow 90. This vertical run-out becomes critical at certain critical stations disposed around the circumference of rotor 54, of which vessel-wash probe 78 is exemplary. As shown in FIG. 3, when a vessel C is rotated, arrow 100, into position under probe 78, the liquid already therein, including patient sample, is aspirated out by a pump 102, after the probe has been lowered into the vessel, arrow 104. Thereafter, wash water is supplied from reservoir 106 at least once, and a final wash is dispensed to an excessive level "A" in a rough dispensing step. A fine adjustment is then used in pump 102 to aspirate out to a known fixed level B, providing an accurate volume of soak liquid, e.g., 230 µL, for soaking the reactive complexes inside the vessel C for an incubation period.

However, such accurate volume presumes that there has been zero vertical run-out, arrow 90. Since, however, this is not the case, positioning the exterior surface 110 of probe 78 at level "B" will not ensure an accurate predetermined soak volume, since the height of the vessel C when empty is no longer predetermined.

Figure 4:
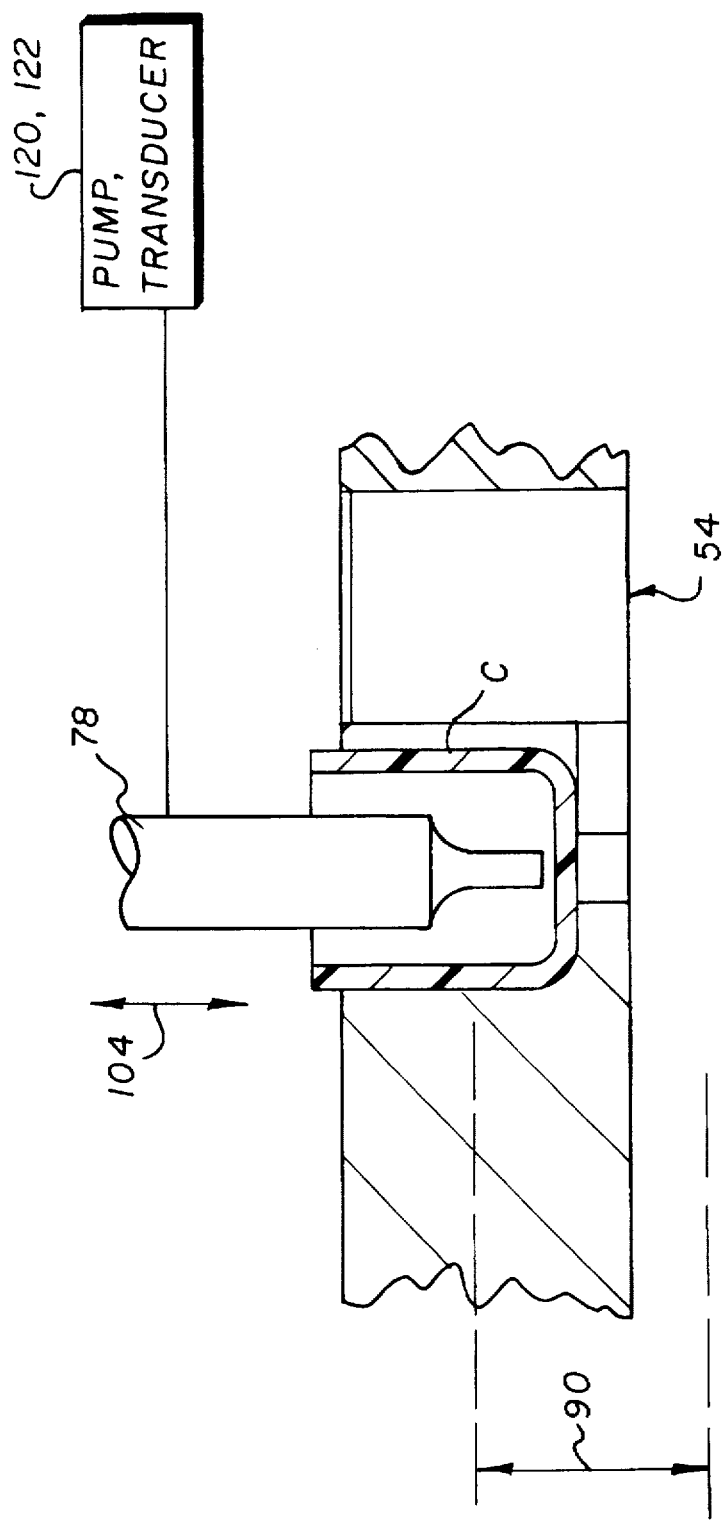
FIG. 4 is a fragmentary elevational view similar to that of FIG. 3, but of an alternative embodiment.

In accordance with the invention, this is corrected by providing a sensing probe and step wherein the empty or "tare" height of each vessel in the rotor, while in an aperture 70, is determined at the time of machine set-up, as the rotor rotates past a critical station (in this case, the vessel-wash station 78). This is done by sensing a reference surface of the vessel. That reference surface comprises either horizontal surface 56 immediately adjacent one or both sides of each vessel, as shown in FIG. 3, or the bottom of the empty vessel C itself as shown in FIG. 4. That is, vessel-wash probe 78 is outfitted with a source of air pressure 120 and a pressure transducer 122, connected via a one-way valve 124 that allows air flow in the direction of arrow 126, but no liquid flow opposite to arrow 126 back to source 120 or transducer 122. As probe 78 lowers towards surface 56, arrow 79, at a certain minimum distance from the surface the build-up of air will exceed a threshold value in transducer 122, indicating the presence of surface 56 at a known height, recorded in the analyzer's computer. The downward advance of probe 78 ceases at this point. This technique is more fully described in, e.g., U.S. Pat. No. 4,794,085, wherein the surface detected is a liquid. As indicated, the height of surface 56 at either side of vessel C can be used, or an average of the two. The process is then repeated by rotating rotor 54, arrow 100, until the next vessel C (not shown) is brought into position adjacent probe 78, and the tare height-sensing process is then repeated. This is done for all the vessels at all the apertures 70, FIG. 2, in the entire annulus of rotor 54, because the amount of vertical run-out 90 at station 78 may vary for each such aperture 70. The computer, of course registers what the tare height is for each such location, to adjust the depth the probe 78 must extend during vessel washing to provide an effective location B for tip surface 110 that gives the same volume of remaining soak liquid, regardless of the vertical run-out 90.

Alternatively, as shown in FIG. 4, probe 78 can extend down to the bottom of empty vessel C to detect the reference surface of the vessel, in a manner otherwise identical to the procedure described above for FIG. 3.

Figure 5:
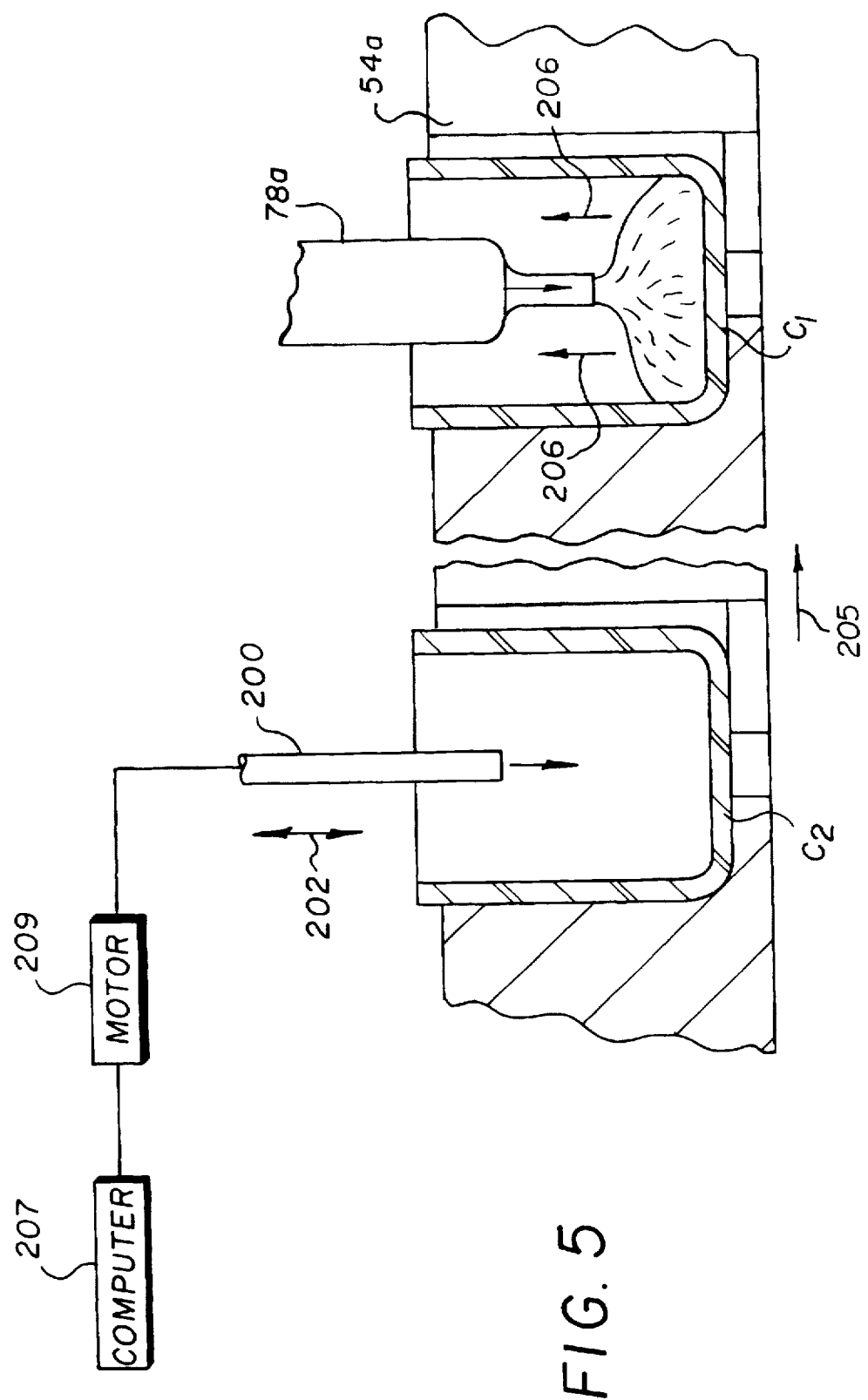
FIGS. 5 and 6 are views similar to that of FIG. 4, but of yet another alternative embodiment, showing the sequence of steps therefor.

FIG. 5 illustrates several features of the invention. For one thing, a sensing probe independent of vessel wash probe 78 can be used to determine the tare height, especially of the bottom of each empty vessel. Parts similar to those previously described bear the same reference numeral, to which the distinguishing suffix "a" is appended. It will be appreciated that this embodiment assumes the analyzer configuration is such that enough room is provided for the sensing probe to operate adjacent to the vessel-washing probe, by moving down into and up out of each vessel.

Thus, FIG. 5, rotor 54a carries vessels $C_1, C_2, \ldots C_n$ past a critical station, preferably the vessel aspirate-and-wash station using probe 78a, as before. However, in this case, probe 78a has no air pressure source or transducer connected to it. Instead, such are connected in the same way (not shown) to a sensor 200, which is a simple tube, mounted for vertical movement, arrow 202, much as is mounted probe 78a for vertical movement. (Preferably, both probe 78a and sensor 200 also pivot out away from vertical alignment with rotor 54a, when not in use, e.g., via conventional mechanisms such as motor 209 and any suitable linkage, for sensor 200.) The air delivered by sensor 200, arrow 204 is sufficient to detect the tare height of the empty vessel underneath it, for all such vessels $C_1, C_2 \ldots C_n$, during machine set-up, thus registering in the computer (e.g., computer 207) the vertical run-out effect for that portion of the rotor supporting that particular vessel. Because of the close proximity to probe 78a, any vessel thereafter, arrow 205, can be moved so as to be washed, arrows 206, e.g., vessel $C_1$ as shown, relying on the tare height determined by sensor 200 to cause an accurate soak volume to be left behind by probe 78a.

Figure 6:
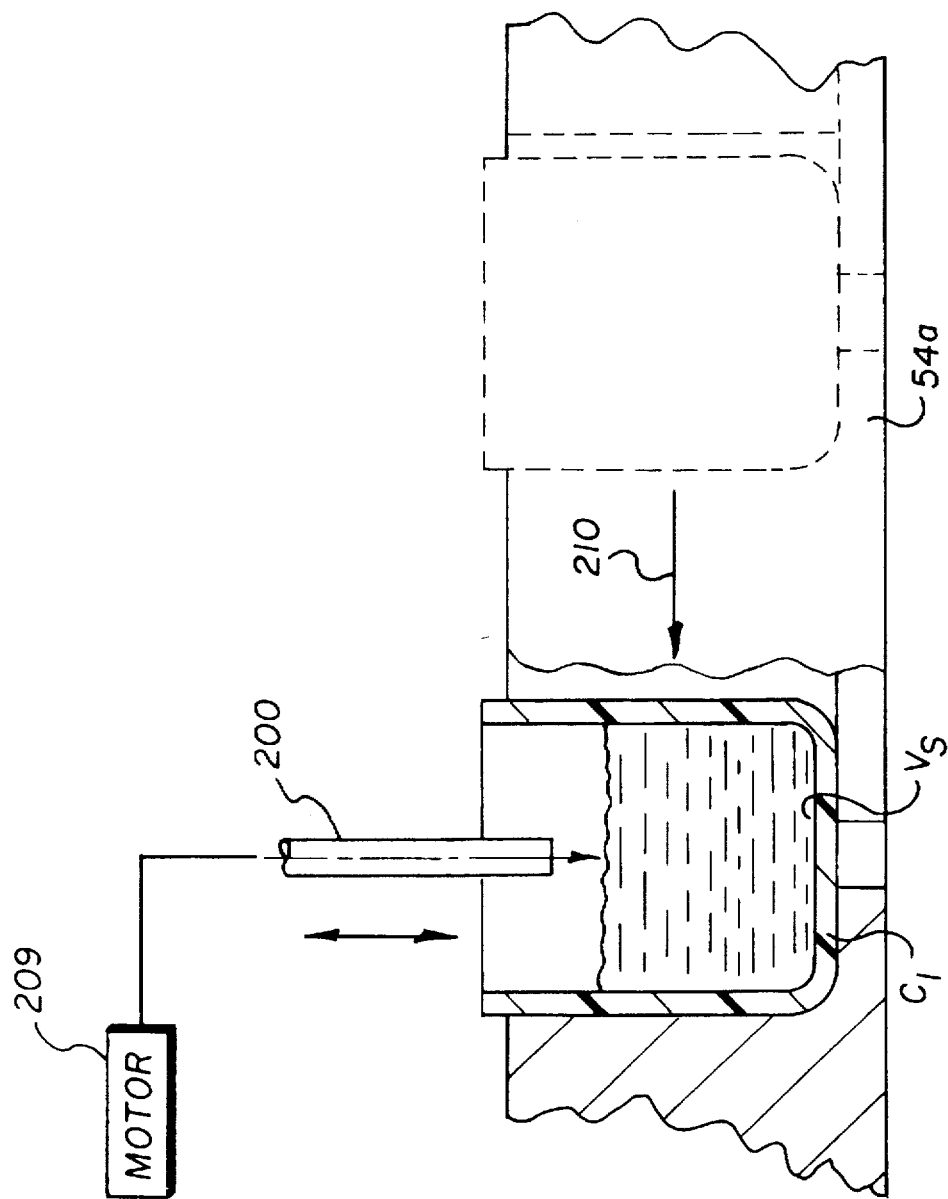

The sensor of FIG. 5 can have an alternative, independent usage. That is, it is possible for probe 78a to also include its source of air pressure and transducer, as well as sensor 200. Each air pressure source and transducer can be separate from the other, or the same source and transducer can be used for both. In either case, the function of sensor 200 is to provide an independent check on the performance of probe 78a in its aspiration and re-soaking of each vessel. In such a case, sensor 200 need not be located anywhere near probe 78a (not shown) around the rotor circumference. In such a procedure, sensor 200 determines the tare height of each empty vessel during machine set-up, FIG. 5, as described above. Then, FIG. 6, after probe 78a has aspirated and left behind soak volume Vs, the pertinent vessel (here $C_1$) is moved back, arrow 210 to sensor 200 which then moves down to sense the height of the liquid present, by sensing the air-liquid interface. The tare height originally determined is subtracted from the just-sensed liquid height, and the analyzer computer converts the differences in heights to a volume measurement for that vessel $C_1$, given that the dimensions of the vessel are pre-known and pre-entered into the computer. This determined volume measurement is then compared with the "prescribed" volume pre-set for the analyzer, to be certain it is within acceptable variations of that prescribed volume. If it is not, then an error flag is created to indicate that probe 78a is not functioning properly.

The reason for using sensor 200 in such a case to determine the liquid height, instead of probe 78a which also has that capability, is that it is not proper protocol to test the performance of an analyzer part (probe 78a) by using that very part being verified.

In all instances of the embodiments described above, the probe or sensor never contacts the surface that is to be detected, thus avoiding the risk of contamination.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of determining the volume of liquid added to a reaction vessel of known dimensions, comprising the steps of:
   a) positioning the vessel in a movable support;
   b) moving the support and vessel until the vessel is at a sensing station;
   c) sensing the vertical position of the bottom inside surface of the vessel at said sensing station by expelling air from a sensor fluidly connected to a pressure transducer, and detecting a pressure change when the expelled air encounters said inside surface;
   d) moving said support and vessel to a liquid-adding station;
   e) adding a volume of liquid to the vessel at said liquid-adding station, leaving an air-liquid interface at the top of said volume;
   f) moving said support and vessel until the vessel is returned to said sensing station;
   g) sensing the vertical position of said interface at said sensing station by expelling air from said sensor and detecting a pressure chance in said transducer when the expelled air encounters said air-liquid interface; and
   h) converting the sensed vertical positions of said bottom surface and said interface into a volume measurement of said liquid volume.

2. A method as defined in claim 1, wherein said sensing is done without contacting said bottom surface or said interface with said sensor.

3. A method as defined in claim 1 or 2, wherein said sensor is an air nozzle fluidly connected to a source of pressurized air and a pressure transducer.

* * * * *

UNITED STATES PATENT AND TRADEMARK OFFICE
CERTIFICATE OF CORRECTION

PATENT NO. : 5,753,512

DATED : November 19, 1998

INVENTOR(S) : James Daniel Riall
David Donald Hyde

It is certified that error appears in the above-identified patent and that said Letters Patent is hereby corrected as shown below:

Column 6, Line 26, should read --detecting a pressure change in said transducer when the--.

Signed and Sealed this

Twenty-ninth Day of September, 1998

Attest:

BRUCE LEHMAN

*Attesting Officer*         *Commissioner of Patents and Trademarks*